US010499560B1

(12) United States Patent
Bissell et al.

(10) Patent No.: US 10,499,560 B1
(45) Date of Patent: Dec. 10, 2019

(54) METHODS OF USING DRIFT REDUCTION ADJUVANT COMPOSITIONS

(71) Applicant: Winfield Solutions, LLC, Shoreview, MN (US)

(72) Inventors: Daniel Bissell, Eagan, MN (US); Lee Boles, River Falls, WI (US); Andrea Clark, River Falls, WI (US)

(73) Assignee: WINFIELD SOLUTIONS, LLC, Arden Hills, MN (US)

( * ) Notice: Subject to any disclaimer, the term of this patent is extended or adjusted under 35 U.S.C. 154(b) by 0 days.

(21) Appl. No.: 16/198,384

(22) Filed: Nov. 21, 2018

(51) Int. Cl.
A01N 25/24 (2006.01)
A01C 21/00 (2006.01)
A01M 7/00 (2006.01)
A01N 25/04 (2006.01)

(52) U.S. Cl.
CPC ........... A01C 21/00 (2013.01); A01M 7/0042 (2013.01); A01N 25/04 (2013.01)

(58) Field of Classification Search
None
See application file for complete search history.

(56) References Cited

U.S. PATENT DOCUMENTS

| 6,607,146 B1* | 8/2003 | Alness | A01M 7/0064 239/159 |
| 8,689,619 B2 | 4/2014 | Spandl et al. | |
| 2009/0241817 A1* | 10/2009 | Eastin | A01C 1/06 111/118 |
| 2015/0150249 A1* | 6/2015 | Nolte | A01N 37/40 504/362 |
| 2016/0192642 A1* | 7/2016 | Lindner | A01N 57/20 504/204 |
| 2016/0374334 A1* | 12/2016 | Di Modugno | A01N 25/30 504/206 |
| 2017/0006859 A1* | 1/2017 | Raman | A01N 25/30 |
| 2017/0042142 A1* | 2/2017 | Baur | A01N 25/24 |
| 2017/0238536 A1* | 8/2017 | Goyal | A01N 25/24 |
| 2017/0258078 A1* | 9/2017 | Costa | A01N 25/30 |
| 2018/0055045 A1* | 3/2018 | Baur | A01N 25/02 |
| 2018/0077927 A1* | 3/2018 | Bonn | A01N 25/00 |
| 2018/0184647 A1* | 7/2018 | Bissell | A01N 25/06 |
| 2019/0037836 A1* | 2/2019 | Bissell | A01N 25/02 |

OTHER PUBLICATIONS

Ng, C.-L. et al. "Bag breakup of nonturbulent liquid jets in crossflow." International Journal of Multiphase Flow 34 (2008) pp. 241-259.
ANSI/ASABE S592.1, "Best Management Practices for Boom Spraying", American Society of Agricultural and Biological Engineers, Aug. 2016, 14 pages.

* cited by examiner

Primary Examiner — Andre J Allen
(74) Attorney, Agent, or Firm — Dorsey & Whitney LLP

(57) ABSTRACT

A method to reduce bag rupture in an agricultural spray dispensed from a nozzle is disclosed. The method includes dispensing the agricultural spray from the nozzle. The agricultural spray includes water, at least one polymer, and at least one perforation-aid type adjuvant. The agricultural spray exhibits fewer fine droplets exhibiting a diameter less than about 150 µm formed via the bag rupture approach to droplet formation.

21 Claims, 3 Drawing Sheets

METHODS OF USING DRIFT REDUCTION ADJUVANT COMPOSITIONS

CROSS-REFERENCE TO RELATED APPLICATIONS

This application is filed concurrently with U.S. patent application Ser. No. 16/198,349, filed Nov. 21, 2018, entitled "Test Sections, Wind Tunnels Including the Same, and Methods of Using the Same," now U.S. Pat. No. 10,359,337, which is herein incorporated by reference in its entirety for any useful purpose.

TECHNICAL FIELD

The present disclosure related to products, systems, and methods of using adjuvant compositions in agricultural spray applications, and more particularly, to drift reduction adjuvant compositions for such applications.

BACKGROUND

Crop protection and cultivation practices commonly involve the application of agricultural sprays. These sprays may contain a variety of components including pesticides for combatting pests such as insects, weeds, and fungus. However, these pesticides can cause environmental problems when the agricultural spray experiences drift and fails to reach the intended target. This has raised an increasing level of concern about pest control costs and environmental pollution associated with agricultural sprays. As a result, application of such sprays requires precision and care. Considerable research on spray drift has been conducted, but it remains a major problem associated with many agricultural spray applications. Consequently, there is a need to provide drift reduction technologies for use with agricultural sprays.

SUMMARY

In an embodiment, a method to reduce bag rupture in an agricultural spray dispensed from a nozzle is disclosed. The method comprises dispensing the agricultural spray from the nozzle. The agricultural spray comprises water, at least one polymer, and at least one perforation-aid type adjuvant. The agricultural spray exhibits fewer fine droplets exhibiting a diameter less than about 150 μm formed via the bag rupture approach to droplet formation than a substantially similar agricultural spray that does not comprise the at least one perforation-aid type adjuvant as determined by an analysis of the agricultural spray. The analysis of the agricultural spray comprises detecting at least a portion of the agricultural spray adjacent to the nozzle or a substantially similar nozzle such that one or more bags rupturing from the agricultural spray, if present, are detected. Each of the one or more bags comprise a thin membranes semi-spherical protrusion extending from the agricultural spray. The portion of the agricultural spray adjacent to the nozzle includes a region of the agricultural spray initially exiting the nozzle that forms a continuous sheet-like portion defining an initial spray pattern.

In an embodiment, a method to reduce bag rupture in an agricultural spray dispensed from a nozzle is disclosed. The method comprises dispensing the agricultural spray from the nozzle. The agricultural spray exhibits a generally sheet-like shape. The agricultural spray comprises water, at least one drift reduction adjuvant composition comprising at least one rheology modifier and at least one perforation-aid type adjuvant, and at least one agricultural composition comprising at least one pesticide and/or at least one fertilizer. The agricultural spray exhibits fewer fine droplets exhibiting a diameter less than about 150 μm formed via the bag rupture approach to droplet formation than a substantially similar agricultural spray that does not comprise the at least one perforation-aid type adjuvant as determined by an analysis of the agricultural spray. The analysis of the agricultural spray comprises detecting at least a portion of the agricultural spray adjacent to the nozzle or a substantially similar nozzle such that one or more bags rupturing from the agricultural spray, if present, are detected. Each of the one or more bags comprise a thin membranes semi-spherical protrusion extending from the agricultural spray. The portion of the agricultural spray adjacent to the nozzle includes a region of the agricultural spray initially exiting the nozzle that forms a continuous sheet-like portion defining an initial spray pattern.

In an embodiment, a method to reduce bag rupture in an agricultural spray dispensed from a flat-fan nozzle is disclosed. The method comprises dispensing the agricultural spray from the flat-fan nozzle in a direction that is substantially perpendicular to a ground. The agricultural spray comprises water, at least one rheology modifier, at least one perforation-aid type adjuvant, and at least one agricultural composition. The at least one rheology modifier comprises at least one of guar gum, modified guar gum, polyacrylamide, or lecithin. The at least one perforation-aid type adjuvant comprises at least one surfactant and at least one of a seed oil, modified seed oil, or a paraffinic oil. The at least one agricultural composition comprises at least one pesticide and/or at least one fertilizer. The agricultural spray exhibits at least 50% fewer fine droplets exhibiting a diameter less than about 150 μm formed via the bag rupture approach to droplet formation than a substantially similar agricultural spray that does not comprise the at least one perforation-aid type adjuvant as determined by an analysis of the agricultural spray. The analysis of the agricultural spray comprises detecting at least a portion of the agricultural spray adjacent to the nozzle or a substantially similar nozzle such that one or more bags rupturing from the agricultural spray, if present, are detected. Each of the one or more bags comprise a thin membranes semi-spherical protrusion extending from the agricultural spray. The portion of the agricultural spray adjacent to the nozzle includes a region of the agricultural spray initially exiting the nozzle that forms a continuous sheet-like portion defining an initial spray pattern.

In various implementations and alternatives, the at least one polymer comprises at least one rheology modifier.

In various implementations and alternatives, the at least one rheology modifier includes at least one of guar gum, modified guar gum, polyacrylamide, or lecithin.

In various implementations and alternatives, the at least one polymer comprises lecithin.

In various implementations and alternatives, the at least one perforation-aid type adjuvant comprises at least one oil emulsion and at least one surfactant.

In various implementations and alternatives, the at least one oil emulsion comprises at least one modified seed oil.

In various implementations and alternatives, the at least one perforation-aid type adjuvant forms about 0.04% (v/v) to about 1.0% (v/v) of the agricultural spray.

In various implementations and alternatives, the at least one perforation-aid type adjuvant comprising a suspension type herbicide.

In various implementations and alternatives, the at least one perforation-aid type adjuvant comprises at least one non-ionic surfactant.

In various implementations and alternatives, the agricultural spray comprises at least one agricultural composition, the at least one agricultural compositing including at least one pesticide and/or at least one fertilizer.

In various implementations and alternatives, dispensing the agricultural spray from the nozzle comprises dispensing the agricultural spray from a nozzle in a direction that is generally perpendicular to the ground.

In various implementations and alternatives, dispensing the agricultural spray from the nozzle comprises dispensing the agricultural spray from the nozzle in a generally vertical direction and exposing the agricultural spray to air flowing in a direction that is generally parallel to ground.

In various implementations and alternatives, the agricultural spray is dispensed from the nozzle in a generally sheet-like shape and the air flowing in the direction that is generally parallel to ground intersects the generally sheet-like shape of the agricultural spray at an oblique angle.

In various implementations and alternatives, dispensing the agricultural spray from the nozzle comprises analyzing the agricultural spray by dispensing the agricultural spray in an enclosed space of a test section of a wind tunnel. Analyzing the agricultural spray further comprises emitting a stimulus into the enclosed space towards at least a portion of the agricultural spray adjacent to the nozzle and detecting at least the portion of the agricultural spray adjacent to the nozzle.

In various implementations and alternatives, dispensing the agricultural spray from the nozzle comprises dispensing the agricultural spray from a ground applicator that includes the nozzle, the ground applicator moving at a speed of about 20 miles per hour or less.

In various implementations and alternatives, the agricultural spray exhibits at least 50% fewer of the fine droplets formed via the bag rupture approach to droplet formation than the substantially similar agricultural spray that does not comprise the at least one perforation-aid type adjuvant.

In various implementations and alternatives, the agricultural spray exhibits at least 90% fewer of the fine droplets formed via the bag rupture approach to droplet formation than the substantially similar agricultural spray that does not comprise the at least one perforation-aid type adjuvant.

In various implementations and alternatives, the nozzle is a flat-fan nozzle.

Features from any of the disclosed embodiments may be used in combination with one another, without limitation. In addition, other features and advantages of the present disclosure will become apparent to those of ordinary skill in the art through consideration of the following detailed description and the accompanying drawings.

BRIEF DESCRIPTION OF THE DRAWINGS

The drawings illustrate several embodiments of the present disclosure, wherein identical reference numerals refer to identical or similar elements or features in different views or embodiments shown in the drawings.

DETAILED DESCRIPTION

Figure 1A:
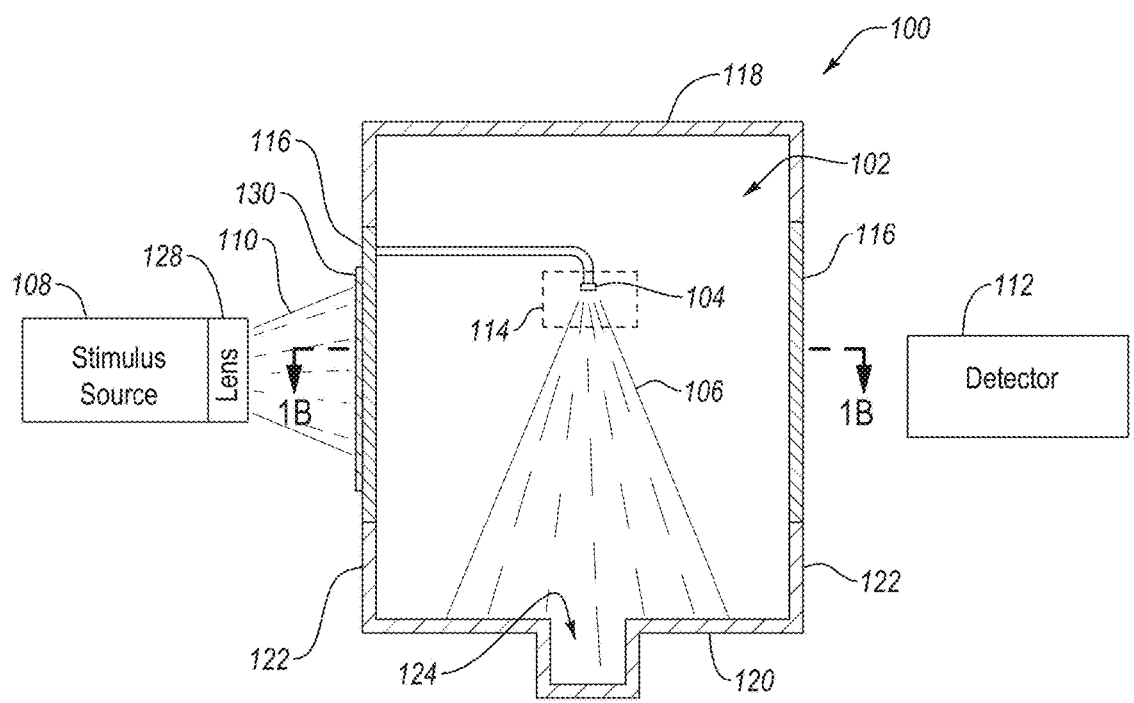
FIGS. 1A and 1B are cross-section and top plan views, respectively, of a test section, according to an embodiment.

Within agricultural field applications, disadvantageous spray attributes exist. Often, fine droplets are produced which are susceptible to off-target drift. Drifting fine droplets (e.g., v150 or driftable fine droplets<150 µm), i.e., "drift", can deposit on unintended plant surfaces causing injury or harm to the vegetation. Furthermore, traditional measures of reducing the spray volume composition of fine droplets having a diameter less than 150 µm ("fine droplets", e.g., "fines"), by way of nozzle design or chemical adjuvant additive, often increases the volume composition of extra-large droplets (e.g., v622 or ultra-coarse droplets>622 µm). Significantly high rates of ultra-coarse droplets having a diameter greater than 622 µm ("ultra-coarse droplets") diminishes the area coverage of the agrochemical pesticide product. Reduced area coverage has been linked to reduced efficacy of the product performance, and the evolution of chemical-resistance in commonly-treated weed species. In either case, significant quantities of small or ultra-coarse droplets within the spray volume can hinder the performance of the applied agrochemical products.

The number of fine droplets and/or ultra-coarse droplets can depend on the atomization mechanism that forms the droplets. It was previously believed that spray sheets formed from flat fan nozzles, the most common nozzle class in agricultural applications, and other types of nozzles were dominated by two atomization mechanisms: the wave instability and perforation approaches of droplet formation. For the wave instability approach, ligament formation may be produced by aerodynamically-induced wave instabilities. These instabilities grow to generate wave fronts within the spray sheet region just downstream of the nozzle outlet. These wave fronts form continuous thick and thin bands that extend the spray sheet region farther downstream from the nozzle. The thin bands eventually collapse, forming ligaments from the thick bands, which in turn collapse into droplets. Alternatively, in the perforation approach, the spray sheet may perforate, generating voids within the spray sheet which grow to form a web-like structure of ligaments. This ligament structure eventually continues to collapse into droplets. Regardless of the atomization mechanism for these spray sheets, a wide geometric spectrum of droplet sizes is produced.

The droplet size of the spray sheets can be managed (i.e., the number of smaller particles are reduced, and the number of ultra-coarse particles are reduced, maintained, or slightly increased) by adding adjuvant compositions to the agricultural spray that form the spray sheets. The adjuvants are configured to effect the wave instability and perforation atomization approaches. Two such adjuvants includes the adjuvants disclosed in U.S. patent application Ser. No. 15/857,145 filed on Dec. 28, 2017 and U.S. patent application Ser. No. 16/023,790 filed on Jun. 29, 2018, the disclosure of each of which is incorporated herein, in its entirety, by this reference.

It has recently been discovered that previous drift reduction adjuvant compositions that include at least one polymer (e.g., rheology modifier) unexpectantly resulted in a large number of fine droplets under certain conditions. For example, the previous drift reduction adjuvant compositions that included at least one polymer were tested in wind tunnels under conditions that examined the previous drift reduction adjuvant compositions' ability to prevent formation of fine droplets due to the wave stability and perforation approaches of droplet formation. Examples of such wind tunnels are disclosed in ANSI/ASABE S592.1 published in the American Society of Agricultural and Biological Engineers and U.S. Pat. No. 8,689,619 filed on Sep. 13, 2012, the disclosure of each of which is incorporated herein, in its entirety, by this reference. The composition and quantity of the polymer in the previous drift reduction adjuvant compositions were selected, at least in part, based on these tests performed in the wind tunnel. However, applying agricultural sprays outdoors (e.g., in the field) that included the previous drift reduction adjuvant compositions, under certain circumstances, resulted in a greater than expected number of fine droplets.

In an attempt to determine the cause of the greater than expected number of fine droplets when the agricultural spray was applied outdoors, it was recently discovered that a third atomization mechanism can cause the formation of fine droplets: the bag rupture approach to droplet formation caused by the presence of the polymer in the drift reduction adjuvant composition (e.g., a spray tank composition that includes the drift reduction adjuvant composition). The bag rupture approach is caused by the formation of a continuous liquid phase in a spray sheet near the nozzle. A portion of the continuous liquid phase of the spray sheet is subjected to hydrodynamic forces associated with the fluid discharge and certain surrounding aerodynamic forces of the environment which can result in a formation of a thin membraned semi-spherical protrusion extending from the agricultural spray (e.g., extending from the continuous liquid phase of the spray sheet), which is referred to as a "bag" herein. Upon rupture, the thinnest portion of the bag membrane atomizes thereby generating a large number of fine droplets that are ejected in a direction generally perpendicular to the spray sheet. These fine droplets are susceptible to drift because the fine droplets trajectories are aligned with the environmental wind conditions (i.e., not oriented toward the target location) and the fine droplets are dominated by environmental forces (e.g., aerodynamic forces) and not by gravitational forces. The remainder of the bag membrane further collapse into various ligament geometries and contrails. In an example, circumstances that can cause the bag rupture approach includes air movement around the continuous liquid phase of the spray sheet induced by a combination of atmospheric wind conditions and/or travel speed on an applicator of the agricultural spray (i.e., the speed that a tractor or other device that includes the nozzle moves relative to a ground surface), or a spray sheet discharging in a direction perpendicular to the surrounding air flow.

I. Drift Reduction Adjuvant Compositions

According to implementations, drift reduction adjuvant compositions (also known as drift reduction adjuvants and drift reduction technology, drift and deposition aids, or drift additives) disclosed herein comprise atomization modifiers for modifying the formation of droplets product through all three of wave instability, perforation, and bag rupture approaches to droplet formation. The drift reduction adjuvant compositions include at least one polymer (e.g., at least one rheology modifier) and at least one perforation-aid type adjuvant. The polymer, and more particularly the rheology modifier, can be included in the drift reduction adjuvant composition for targeting the wave instability approach to droplet formation. Targeting the wave instability approach of droplet formation allows the polymer, and more particularly the rheology modifier, to reduce the number of fine droplets that are formed while, inadvertently, also increasing the number of ultra-coarse particles that are formed. However, as previously discussed, the presence of the polymer can, under certain circumstances, also inadvertently cause the drift reduction adjuvant to form more fine droplets due to the bag rupture approach of droplet formation. The perforation-aid type adjuvant in the drift reduction adjuvant targets the perforation and bag rupture approaches to droplet formation. For example, taking the perforation approach to droplet formation into consideration, the perforation-aid type adjuvant is included in the drift reduction adjuvant to minimize the effect that the polymer, and more particularly the rheology modifier, has on the number of ultra-coarse particles that are formed. Further, the perforation-aid type adjuvant can actually reduce the number of fine droplets that are formed due to the bag rupture approach to droplet formation, which is unexpected since it was previously believed that the perforation-aid type adjuvant merely reduce the average particle size of the droplets formed in the agricultural spray (e.g., decrease the number of ultra-coarse droplets). The perforation-aid type adjuvant can reduce the number of fine droplets, under certain circumstances, because the perforation-aid type adjuvant causes the spray sheet of the agricultural spray to exhibit less bag rupture. As used herein, "less bag rupture" refers to forming fewer fine droplets via the bag rupture approach to droplet formation using any of the drift reduction adjuvants disclosed herein. Not wishing to be bound by theory, it is currently believed that the perforation-aid type adjuvant causes the agricultural spray to exhibit less bag rupture because the perforation-aid type adjuvant causes any bags that are formed in the spray sheet to prematurely rupture before the bags atomize thereby reducing or eliminating the number of small particles formed from the bags.

In an embodiment, selecting the compositions and quantities of the polymer and the perforation-aid type adjuvant, taking only the wave instability and perforation approaches into consideration, may not result in less bag rupture. For example, as previously discussed, the presence of the polymer in the drift reduction adjuvant can cause bags to form in the continuous liquid phase of the spray sheet. However, the composition and quantities of the polymer and the perforation-aid type adjuvant can be selected while also taking into consideration the bag rupture approach to droplet formation. Taking into consideration the bag rupture approach to droplet formation can consider the wind speed, the angle of the wind relative to the spray sheet, the travel speed of the applicator that includes the nozzle, the angle that the applicator is moving relative to the spray sheet, the nozzle type, the composition and quantity of the polymer that is present in the drift reduction adjuvant composition, the composition and quantity of the perforation-aid type adjuvant that is present in the drift reduction adjuvant composition, etc. In an example, taking into consideration the bag rupture approach of droplet formation can include decreasing and/or increasing the quantity of the polymer or the perforation-aid type adjuvant, respectively, that is in the drift reduction adjuvant composition compared to a drift reduction adjuvant composition that only took into consideration the wave stability and perforation approach to droplet formation. In an example, taking into consideration the bag rupture approach to droplet formation can include selecting a composition of a polymer that is likely to cause less bag rupture than another polymer. In an example, taking into consideration the bag rupture approach to droplet formation can include selecting a composition of the perforation-aid type adjuvant that is likely to decrease the polymer's ability to generate bags in the continuous liquid phase of the spray sheet than another perforation-aid type adjuvant.

In an embodiment, an agricultural spray that includes any of the drift reduction adjuvants disclosed herein can have less bag rupture when the agricultural spray is dispensed from a nozzle than a substantially similar agricultural spray that does not include the drift reduction adjuvants disclosed herein delivered under the same conditions (e.g., delivered from the same nozzle at the same pressure and flow rate). It is noted that the substantially similar agricultural spray that does not include the drift reduction adjuvants disclosed herein can include at least one of a drift reduction adjuvant that does not include at least one perforation-aid type adjuvant or a drift reduction adjuvant that was not selected while taking the bag rupture approach into consideration. For example, the agricultural spray including the drift reduction adjuvant compositions disclosed herein may have at least about 50% less bag rupture, at least about 60% less bag rupture, at least about 70% less bag rupture, at least about 80% less bag rupture, at least about 90% less bag rupture, no bag rupture, about 50% to about 70% less bag rupture, about 60% to about 80% less bag rupture, at least 70% to about 90% less bag rupture, or about 80% to about 100% less bag rupture than a substantially similar agricultural that does not comprise the at least perforation-aid type adjuvant. It is noted that the drift reduction adjuvant composition may not necessarily form any of the above reductions in bag rupture if the drift reduction adjuvant composition is formulated without taking the bag rupture approach to droplet formation into consideration.

a. Polymers

As previously discussed, the agricultural sprays disclosed herein can include at least one polymer. The polymer can form part of a drift reduction adjuvant composition that is added to the agricultural spray, or can be distinct from the drift reduction adjuvant composition. The polymer can include at least one rheology modifier or another polymer (e.g., lecithin).

The rheology modifier is selected to effect the wave instability approach of droplet formation. Rheology modifiers may include but are not limited to: polymers, Newtonian-responding polymers, monosaccharides, polysaccharides (e.g., colloidal polysaccharides, starches, vegetable gums, pectin), glucose, fructose, galactose, mannose, lactose, fructose, xylose, amylose, raffinose, maltotriose, glucosides, trehalose, saccharide alcohols (e.g., mannitol, sorbitol, xylitol and maltitol), compositions containing sugar such (e.g., molasses and honey), guar gum (e.g., crop-based guar gum, modified guar gum), xanthan, cellulose, Locust bean, alginate, agar-agar, carrageenan, gum arabic, dimethylpolysiloxane, polyacrylamide, lecithin, and derivatives of and combinations thereof. Newtonian polymers can be characterized by a single coefficient of viscosity or a slight variation of viscosity for a range of shearing or temperature conditions. Traditionally, the viscosity will not significantly change with the rate of applied shear force. Newtonian-responding rheology modifiers may include but are not limited to guar gum, glycerol and/or paraffin waxes or oils.

In an example, the rheology modifier includes at least one of guar gum, modified guar gum, polyacrylamide, or lecithin since such rheology modifiers, combined with a perforation-aid type adjuvant, can be more effective at reducing the number of fine droplets and managing the number of coarse droplets compared to at least some of the other rheology modifiers disclosed herein. Further, the rheology modifier can include at least one of guar gum, modified guar gum, polyacrylamide, or lecithin since such rheology modifiers, when combined with a perforation-aid type adjuvant, can form agricultural sprays exhibiting less bag rupture than at least some of the other rheology modifiers disclosed herein.

The polymer may be present in the drift reduction adjuvant composition a range from about 0.25 to about 6.0% (v/v), about 0.25 to about 0.75% (v/v), about 0.5 to about 1.0% (v/v), about 0.75 to about 1.5% (v/v), about 0.5 to about 5% (v/v), about 0.5 to about 4.0% (v/v), about 0.5 to about 3.0% (v/v), about 0.5% to about 2.0% (v/v), about 1.0 to about 5.0% (v/v), about 1.0 to about 4.0% (v/v), about 1.0 to about 3.5% (v/v), or about 1.0 to about 3.25% (v/v), about 1.0 to about 3.0% (v/v), about 1.0 to about 2.75% (v/v), about 1.25 to about 4.5% (v/v), about 1.5 to about 4.0% (v/v), about 2.0 to about 4.0% (v/v), about 2.0 to about 4.0% (v/v), up to about 6% (v/v), up to about 5.0% (v/v), up to about 4.0% (v/v), up to about 3.5% (v/v), up to about 3.0% (v/v), or up to about 2.0% (v/v) of the adjuvant. Alternatively, the polymer may be present in the drift reduction adjuvant composition at any integer range of the aforementioned levels (e.g., about 1.25 to about 2.75% (v/v) of the drift reduction adjuvant composition. The polymer may be present in the drift reduction adjuvant composition in a range from about 0.0025 to about 0.08 g/ml, about 0.0025 to about 0.0075 g/ml, about 0.005 to about 0.01 g/ml, about 0.0075 to about 0.015 g/m., about 0.0005 to about 0.065 g/ml, about 0.0005 to about 0.05 g/ml, about 0.0005 to about 0.04 g/ml, about 0.0005 to about 0.04 g/ml, about 0.0005 to about 0.02 g/ml, about 0.01 to about 0.065 g/ml, about 0.01 to about 0.06 g/ml, about 0.01 to about 0.05 g/ml, about 0.01 to about 0.04 g/m. about 0.01 to about 0.03 g/ml, about 0.02 to about 0.04 g/ml, about 0.03 to about 0.05, about 0.04 to about 0.06, or about 0.05 to about 0.075. Alternatively, the polymer may be present in the drift reduction adjuvant composition at any integer range of the aforementioned levels (e.g., about 0.00075 to about 0.003 g/ml).

In an embodiment, the polymer may be present in the agricultural spray (e.g., tank-mixed) in a range from about 0.001 to about 0.040% (v/v), about 0.001 to about 0.003% (v/v), about 0.002 to about 0.004% (v/v), about 0.003 to about 0.005% (v/v), about 0.0045 to about 0.036% (v/v), about 0.0045 to about 0.032% (v/v), about 0.006 to about 0.030% (v/v), about 0.008 to about 0.025% (v/v), about 0.009 to about 0.020% (v/v), about 0.009 to about 0.016% (v/v), about 0.009 to about 0.014% (v/v), about 0.009 to about 0.013% (v/v), about 0.009 to about 0.011% (v/v), up to about 0.040% (v/v), up to about 0.035% (v/v), up to about 0.032% (v/v), up to about 0.030% (v/v), up to about 0.025% (v/v), up to about 0.020% (v/v), or up to about 0.016% (v/v) of the agricultural spray. Alternatively, the polymer may be present in the agricultural spray at any integer range of the aforementioned levels (e.g., about 0.009 to about 0.032 (v/v) of the agricultural spray). The polymer may be present in the agricultural spray in a range from about $0.2 \times 10^{-4}$ to about $5 \times 10^{-4}$ g/ml, about $0.2 \times 10^{-4}$ to about $0.5 \times 10^{-4}$ g/ml, about $0.4 \times 10^{-4}$ to about $0.7 \times 10^{-4}$ g/ml, about $0.5 \times 10^{-4}$ to about $1 \times 10^{-4}$ g/ml, about $0.7 \times 10^{-4}$ to about $1.5 \times 10^{-4}$ g/ml, about $0.5 \times 10^{-4}$ to about $3 \times 10^{-4}$ g/ml, about $0.5 \times 10^{-4}$ to about $2 \times 10^{-4}$ g/ml, about $1.0 \times 10^{-4}$ to about $1.4 \times 10^{-4}$ g/ml, about $1.2 \times 10^{-4}$ to about $1.5 \times 10^{-4}$ g/ml, about $1.4 \times 10^{-4}$ to about $1.7 \times 10^{-4}$ g/ml, about $1.5 \times 10^{-4}$ to about $2.0 \times 10^{-4}$ g/ml, about $1.7 \times 10^{-4}$ to about $2.2 \times 10^{-4}$ g/ml, about $2.0 \times 10^{-4}$ to about $2.6 \times 10^{-4}$ g/ml, $2.2 \times 10^{-4}$ to about $2.7 \times 10^{-4}$ g/ml, or about $2.6 \times 10^{-4}$ to about $3 \times 10^{-4}$ g/ml of the agricultural spray. Alternatively, the polymer may be present in the agricultural spray at any integer range of the aforementioned levels (e.g., about $0.7 \times 10^{-4}$ to about $2.0 \times 10^{-4}$ g/ml of the spray).

The amount of the polymer (e.g., rheology modifier such as guar gum or polyacrylamide) in a drift reduction adjuvant composition and/or agricultural spray can be selected to at least one of reduce the number of fine droplets and/or manage the number of the ultra-coarse droplets. As such, the amount of the polymer can be selected based on the desired number of fine droplets and/or ultra-coarse droplets. Typically, when taking the wave stability and perforation approach to droplet formation into consideration, increasing the amount of the polymer, such as increasing the amount of the rheology modifier, decreases the number of fine droplets and increases the number of ultra-coarse droplets. However, depending on certain circumstances, increasing the amount of polymer that is present in the drift reduction adjuvant composition can increase the number of fine droplets since the polymer can cause the bag rupture approach to droplet formation. The amount of the polymer can also be selected based on the amount of the perforation-aid type adjuvant that is present in the drift reduction adjuvant composition and/or the agricultural spray. For example, typically, increasing the amount of the perforation-aid type adjuvant in the drift reduction adjuvant composition and/or the agricultural spray can allow for an increased amount of the polymer in the drift reduction adjuvant composition and/or the agricultural spray. However, the polymer in combination with the perforation-aid type adjuvant can have certain compositions (e.g., sweet spots) where increasing or decreasing the amount of the polymer and/or the perforation-aid type adjuvant can increase the number of fine droplets and/or the number of ultra-coarse droplets. Additionally, the amount of the polymer can be selected based on the type of agricultural nozzle used to spray the agricultural spray and the type of agricultural composition that is mixed with the drift reduction adjuvant composition.

b. Perforation-Aid Type Adjuvant

The perforation-aid type adjuvant of the drift reduction adjuvant composition is selected to effect the wave instability and bag rupture approaches of droplet formation. In an embodiment, the perforation-aid type adjuvant can include at least one oil and/or a polymer solution along with an emulsifier. In an embodiment, the perforation-aid type adjuvant can include an agricultural composition, such as pesticide or a suspension-type herbicide. In an embodiment, the perforation-aid type adjuvant can be mixed with the polymer (e.g., rheology modifier) before, during, or after adding the perforation-aid type adjuvant in the agricultural spray.

As previously discussed, the perforation-aid type adjuvant can include at least one oil along with an emulsifier. Oils that may be included in the adjuvant composition of the present disclosure may include but are not limited to: vegetable oil, modified vegetable oil, seed oil, modified seed oil ("MSO"), modified soybean oil (e.g., soybean oil methyl ester, methyl soyate)), modified palm oil, modified rapeseed oil, crop oil concentrate, petroleum hydrocarbons, mineral oil, paraffinic oil, naphthenic oil, aromatic oil, emulsified petroleum distillates, unsaturated fatty acids, paraffin oil, tall oil (e.g., fatty acids of tall oil), phytoblend-based oil, or tallow oil (e.g., tallow fatty acid amine ethoxylated). Modified oils may include oils that are, for instance, methylated, ethylated, propylated, or butylated. In a preferred embodiment, the oil can include seed oil, MSO (e.g., methylated seed oil), or paraffinic oil since such oils may reduce the number of ultra-coarse droplets and minimize the ability of the polymer (especially guar gum, modified guar gum, polyacrylamide, and/or lecithin) to generate droplets via the bag rupture approach to droplet formation that other oils.

In an embodiment, the perforation-aid type adjuvants disclosed herein can include polymers which may be used to supplement or substitute the oils provided herein. The polymers may include but are not limited to: suspended latex, poly(ethylene glycol), poly(vinyl alcohol), polyacrylates, polyacrylamide, poly(vinyl acetate-alt-maleic anhydride), polylactic acid, polyhydroxyalkanoates, and/or polyoxyalkylenes.

The perforation-aid type adjuvant oil, polymer or combinations thereof may be present in the drift reduction adjuvant compositions in a range from about 20 to about 60% (v/v), about 25 to about to about 40% (v/v), about 25 to about to about 35% (v/v), about 30 to about to about 40% (v/v), about 30 to about 50% (v/v), about 40 to about 60% (v/v), up to about 35% (v/v), up to about 40% (v/v), up to about 50% (v/v), or up to about 60% (v/v). Alternatively, the oil, polymer or combinations may be present in the drift reduction adjuvant compositions at any integer range of the aforementioned levels, (e.g., about 30 to about 35% (v/v) of the drift reduction adjuvant composition).

The oil, polymer or combinations thereof may be present in an agricultural spray that includes the drift reduction adjuvant composition in a range from about 0.04% (v/v) to 2% (v/v), about 0.05 to about 0.6% (v/v), about 0.06 to about 0.6% (v/v), about 0.07 to about 0.6% (v/v), or about 0.08 to about 0.4% (v/v), about 0.08 to about 0.4% (v/v), about 0.1 to about 0.4% (v/v), about 0.2 to about 0.4% (v/v), about 0.2 to about 0.8% (v/v), about 0.2 to about 1.0% (v/v), about 0.4 to about 1.2% (v/v), about 1 to about 1.5% (v/v), about 1.25 to about 1.75% (v/v), about 1.5 to about 2% (v/v), up to about 2% (v/v), up to about 1.5% (v/v), up to about 1.25% (v/v), up to about 1.0% (v/v) up to about 0.8% (v/v), up to about 0.7% (v/v), up to about 0.6% (v/v), up to about 0.5% (v/v), or up to about 0.4% (v/v) of the agricultural spray. Alternatively, the oil, polymer or combinations thereof may be present in the agricultural spray at any integer range of the aforementioned levels (e.g., about 0.02 to about 0.4% (v/v) of the spray). The oil, polymer or combinations thereof may be present in the agricultural spray including the drift reduction adjuvant composition in a range from about $1 \times 10^{-5}$ to about $7.5 \times 10^{-3}$ g/ml, about $1 \times 10^{-5}$ to about $5 \times 10^{-5}$ g/ml, about $2.5 \times 10^{-5}$ to about $7.5 \times 10^{-5}$ g/ml, about $5 \times 10^{-5}$ to about $1 \times 10^{-4}$ g/ml, about $7.5 \times 10^{-5}$ to about $2.5 \times 10^{-4}$ g/ml, about $1 \times 10^{-4}$ to about $5 \times 10^{-4}$ g/ml, about $2.5 \times 10^{-4}$ to about $7.5 \times 10^{-4}$ g/ml, about $5 \times 10^{-4}$ to about $1 \times 10^{-3}$ g/ml, about $7.5 \times 10^{-4}$ to about $2.5 \times 10^{-3}$ g/ml, about $1 \times 10^{-3}$ to about $5 \times 10^{-3}$ g/ml, $7.5 \times 10^{-5}$ to about $7.5 \times 10^{-3}$ g/ml, $7.5 \times 10^{-4}$ to about $7.5 \times 10^{-3}$ g/ml, $5 \times 10^{-4}$ to about $9 \times 10^{-3}$ g/ml, $5 \times 10^{-3}$ to about $1 \times 10^{-2}$ g/ml, $7.5 \times 10^{-3}$ to about $1.25 \times 10^{-2}$ g/ml, or $1 \times 10^{-2}$ to about $1.5 \times 10^{-2}$ g/ml. Alternatively, the oil, polymer or combinations thereof may be present in the agricultural spray at any integer range of the aforementioned levels (e.g., about $1 \times 10^{-4}$ to about $9 \times 10^{-3}$ g/ml of the spray).

Emulsifiers of the perforation-type aid adjuvant that can be present in the drift reduction adjuvant compositions of the present disclosure may promote dispersion in aqueous or oil solutions. These may include but are not limited to: surfactants; non-ionic surfactants; anionic surfactants; cationic surfactants; petroleum oil, tall oil-based surfactants (e.g., fatty acids of tall oil); alkyl phenol ethoxylate; ethoxylated alcohol; lecithin (e.g., soy lecithin); modified alkanoate; alkylphenol ethoxylate phosphate ester; dimethylpolysiloxane, glycerol, alcohol ethoxylate; alkyl polysaccharides; polyoxyethylene sorbitol; polyoxyethylene sorbitan emulsifiers, including polyoxyethylene sorbitan fatty acid esters, polyoxyethylene 20 sorbital trioleate, polyoxyethylene sorbitan mixed fatty acid esters, polyoxyethylene sorbitan monolaurate, polyoxyethylene sorbitan monooleate, polyoxyethylene sorbitan monopalmitate, polyoxyethylene sorbitan monostearate, polyoxyethylene sorbitan monotallate, polyoxyethylene sorbitol hexaoleate, polyoxyethylene sorbitol oleate-laurate, polyoxyethylene sorbitol penta tall oil ester (40 moles), polyoxyethylene sorbitol tetraoleate, and polyoxyethylene sorbitol, mixed ethyl ester, and variations and combinations thereof.

Anionic surfactants may be crop-derived surfactants (e.g., derived from corn and/or rapeseed) configured to emulsify methyl esters, such as C18-C22 methyl esters. The surfactant may be dispersible in water and soluble in organic solvents. Example anionic surfactants include polyoxyethylene sorbitan emulsifiers, including those provided herein, alone or in combination with vegetable oil. In addition or alternatively, other surfactants may include but are not limited to: linear alkylbenzene sulfonate salt, branched alkylbenzene sulfonate, ethoxylated fatty alcohols, ethoxylated castor oil, ethoxylated/propoxylated alcohols and copolymers, ethoxylated fatty acids, sorbitan ester, polysorbate, ethoxylated fatty amine, ethoxylated tristyrylphenol, ethoxylated phosphate esternolamide, ethoxylated nonylphenol, tallow amine ethoxylated, tallow amine, naphthalene sulfonate formaldehyde condensate, alcohol alkoxylate, and tristyrylphenol alkoxylate. The surfactant may optionally contain a solvent such as isobutyl alcohol (CAS #78-83-1) at 5-10% and alkyl benzylsulfonic acid, calcium salt (CAS #84989-14-0) at 10-30% of the surfactant.

Non-ionic surfactants may be crop-derived surfactants, such as commercially available surfactants including but not limited to: Alkyl polysaccharide emulsifiers may be commercially available surfactants and include but are not limited to: Agrimul PG 2069®, available from Henkel Corporation of Ambler, Pa.; APG 325®, available from BASF Corporation of Florham Park, N.J.; and AT Plus 438®, available from Uniqema Surfactant of Wilmington, Del.; APG 911 and APG 810, available from Adjuvants Unlimited. Agrimul PG 2069® is an alkyl polyglycoside non-ionic surfactant and includes alkyl polyglycoside polymers with alkyl chains of nine carbons in a concentration of 20% by weight, ten carbon atoms in a concentration of 40 wt % and eleven carbon atoms in a concentration of 40% wt %. The alkyl polyglycoside, APG 325® has an average degree of polymerization of 1.6, and is considered a non-ionic surfactant. It is non-gelling, biodegradable and soluble in dispersions of high salt concentrations. AT Plus 438® is an alkyl polysaccharide based on glucose and fatty alcohols derived from plant sources.

With respect to the drift reduction adjuvant composition, the emulsifier may be present in a range from about 0.1 to about 10.0% (v/v), about 0.5 to about 2.5% (v/v), about 0.75 to about 2.25% (v/v), about 1.0 to about 2.0% (v/v), about 0.1 to about 4.0% (v/v), about 3.0 to about 5.0% (v/v), about 4.0 to about 7.0% (v/v), about 0.6 to about 10.0% (v/v), up to about 1.5% (v/v), up to about 1.6% (v/v), up to about 2.0% (v/v), up to about 2.5% (v/v), up to about 3.0% (v/v), up to about 3.2% (v/v), up to about 4.0% (v/v), up to about 5.0% (v/v), up to about 6.0% (v/v), up to about 7.0% (v/v), up to about 8.0% (v/v), up to about 9.0% (v/v), or up to about 10.0% (v/v) of the drift reduction adjuvant composition. Alternatively, the emulsifier may be present in the drift reduction adjuvant composition at any integer range of the aforementioned levels, e.g., about 2.5 to about 3.2% (v/v) of the drift reduction adjuvant composition.

With respect to the agricultural spray, the emulsifier may be present in a range from about 0.005 to about 1% (v/v), about 0.005 to about 0.03% (v/v), about 0.005 to about 0.030% (v/v), about 0.01 to about 0.04% (v/v), about 0.01 to about 0.030% (v/v), about 0.01 to about 0.02% (v/v), about 0.02 to about 0.05% (v/v), about 0.04 to about 0.08% (v/v), about 0.06 to about 0.1% (v/v), about 0.08 to about 0.15% (v/v), about 0.1 to about 0.2% (v/v), about 0.15 to about 0.3% (v/v), about 0.25 to about 0.5% (v/v), about 0.4 to about 0.7% (v/v), about 0.6 to about 1.0% (v/v), about 0.015% (v/v), about or up to about 0.020% (v/v), about or up to about 0.030% (v/v), about or up to about 0.040% (v/v), about or up to about 0.10% (v/v), about or up to about 0.20% (v/v), about or up to about 0.50% (v/v), or about or up to about 1.0% (v/v) of the agricultural spray. Alternatively, the emulsifier may be present in the spray at any integer range of the aforementioned levels, e.g., about 0.02 to about 0.04% (v/v) of the spray.

The amount of the perforation-aid type adjuvant (e.g., MSO) in the drift reduction adjuvant composition or the agricultural spray can be selected to at least one of reduce the number of fine droplets and/or manage the number of the ultra-coarse droplets. As such, the amount of the perforation-aid type adjuvant can be selected based on the desired number of fine droplets and/or ultra-coarse droplets or whether the agricultural spray is dispensed in certain circumstances that are likely to cause the bag rupture approach to droplet formation. For example, the amount of the perforation-aid type adjuvant can be selected based on the amount of the polymer (e.g., rheology modifier) that is mixed therewith. The combination of perforation-aid type adjuvant in combination with the polymer can have certain compositions (e.g., sweet spots) where increasing or decreasing the amount of the perforation-aid type adjuvant and/or the polymer can increase the number of fine droplets and/or the number of ultra-coarse droplets. Additionally, the amount of the perforation-aid type adjuvant can be selected based on the type of agricultural nozzle used to spray the drift reduction adjuvant, the type of agricultural composition mixed with the drift reduction adjuvant composition.

c. Other Components of the Drift Reduction Adjuvant Compositions

Stabilizing agents may be optional in the drift reduction adjuvant composition, and may include: additional surfactants such as linear alkylbenzene sulfonate salt, branched alkylbenzene sulfonate, ethoxylated fatty alcohols, ethoxylated castor oil, ethoxylated/propoxylated alcohols and copolymers, ethoxylated fatty acids, sorbitan ester, polysorbate, ethoxylated fatty amine, ethoxylated tristyrylphenol, ethoxylated phosphate esternolamide, ethoxylated nonylphenol, tallow amine ethoxylated, tallow amine, naphthalene sulfonate formaldehyde condensate, alcohol alkoxylate, and tristyrylphenol alkoxylate. Resins or other polymers may also be included.

The drift reduction adjuvant composition may include inert components that include but are not limited to: solvents (e.g., isopropyl alcohol and/or isobutyl alcohol), propylene glycol, and a poly-siloxane foam retardant (Si). These inert components may be nonfunctioning agents, surfactant additives, and/or formulation aids, e.g., for reducing the freezing temperature. Such inert components may be present in a range from about 1 to about 30% (v/v) of the adjuvant composition. Other inert components may include anti-foaming agents or defoamers, which may be present in the composition and may include but are not limited to silicone-based defoamers. These components may be present in a range from about 0.001 to about 1.0% (v/v) of the drift reduction adjuvant composition. Antimicrobials, another category of inert components, may be present in the drift reduction adjuvant composition and may include is are not limited to 1,2-benzisothiazolin-3-one in dipropylene glycol-antimicrobial (e.g., Proxel™ GXL, available from Arch Biocides of Smyrna, Ga.). These components may be present in a range from about 0.01 to about 0.25% (v/v) of the drift reduction adjuvant composition. In some approaches, additional adjuvants may be included in the drift reduction adjuvant composition or the tank and may include Preference® adjuvant, which contains alkylphenol ethoxylate, sodium salts of soya fatty acids and isopropyl alcohol.

The drift reduction adjuvant compositions and other compositions of the present disclosure containing the drift reduction adjuvant composition may consist exclusively of the specifically recited components. In addition or alternatively, the drift reduction adjuvant compositions may be free of components disclosed herein. For instance, the drift reduction adjuvant compositions of the present disclosure may be free of one or more of the described adjuvant components or free of any of the described pesticides or additives. In addition or alternatively, the drift reduction adjuvant compositions may be free of high fructose corn syrup, alginate, lecithin, ammonium sulfate, water conditioning agents, buffering agents, coupling agents and/or antifoam agents. The recited compositions may contain various impurities, but in such amounts so as not to affect the advantageous properties of the inventive drift reduction compositions.

II. Applications of Use

The drift reduction adjuvant compositions may form part of an agricultural spray. The agricultural spray can include at least water, at least one drift reduction adjuvant comprising at least one polymer and at least one perforation-aid type adjuvant, and at least one agricultural composition (e.g., at least one of a pesticide, a fungicide, a herbicide, or a fertilizer). The agricultural spray can be used in connection with agricultural spray applications such as spraying seeds, soil, foliage and fruit. Sprays containing the disclosed drift reduction adjuvant compositions may be delivered using ground and/or aerial spray applications. Application may be during the vegetative state, during planting, and/or after planting to reduce drift and manage the production of ultra-coarse droplets of the agricultural spray.

In some implementations, the drift reduction adjuvant compositions may be provided as an in-can admixture of at least the two different atomization modifiers. In addition or alternatively, the drift reduction adjuvant composition may be contained in a pesticide or other agricultural mixture for use in spray applications. In alternative implementations, the atomization modifiers may be provided separately and admixed just prior to use. Admixing may be conducted under agitation. In addition or alternatively, admixing may take place at about 33 to about 100° F. or at ambient temperatures, e.g., about 70 to 90° F. depending on climate, or may take place under elevated temperatures above 90° F. The drift reduction adjuvant compositions may have a pH of about 5.5 to about 7.5 about 5.5 to about 6.5 or about 6.5 to about 7.5, or about 5.5, 6.0, 6.5, 7.0, or 7.5.

In an embodiment, prior to use, the drift reduction adjuvant compositions can be selected such that the agricultural spray that includes the drift reduction adjuvant compositions exhibits less bag rupture when dispensed from a nozzle than a substantially similar agricultural spray that does not include a substantially similar drift reduction adjuvant composition without the at least one perforation-aid type adjuvant. The drift reduction adjuvant compositions can be selected based on a number of different factors. For example, the drift reduction adjuvant can be selected based on the air speed relative to the spray sheet, the direction of the air speed relative to the spray sheet, the nozzle, the composition of the polymer and/or the perforation-aid type adjuvant, the quantity of the polymer and/or the perforation-aid type adjuvant, etc.

In an embodiment, the drift reduction adjuvant composition can be selected based on the air flow that the spray sheet is exposed ("relative air flow"). For example, an agricultural spray that includes the drift reduction adjuvant compositions can be dispensed from the nozzle in a direction that is a generally vertical direction (e.g., in a direction that is generally perpendicular to the ground) while the relative air flow can flow in a direction that is generally parallel to ground (e.g., a generally horizontal direction). The generally vertical direction of the agricultural spray and the direction of the relative air flow can cause the spray sheet formed from the agricultural spray to exhibit the bag rupture approach to droplet formation. It is noted that the spray sheet may still exhibit the bag rupture approach to droplet formation when at least one of the agricultural spray is dispensed from the nozzle in a generally non-vertical direction or the relative air flow flows in a generally non-vertical direction.

The relative air flow can depend on the ambient air (e.g., crosswind) and the movement of an applicator that includes the nozzle. For example, the speed of the relative air flow and the angle that the relative air flow relative to the spray sheet can depend on the speed of the ambient air, the speed of the application, the direction of the ambient air relative to the spray sheet, and the direction of the movement of the applicator relative to the spray sheet. The amount of bag that are formed in the spray sheet and the amount of droplets that are formed according to the bag rupture approach to droplet formation depends, at least in part, on the speed of the relative air flow and the angle of the relative air flow relative to the spray sheet. For example, increasing the speed of the relative air flow can increase the likelihood that the spray sheet forms bags and that at least some of the droplets are formed according to the bag rupture approach to droplet formation, and vice versa. Similarly, causing the angle of the air flow to be closer to 90° (i.e., the relative air flow perpendicularly intersects the spray sheet) can also increase the likelihood that the spray sheet forms bags and that at least some of the droplets are formed according to the bag rupture approach to droplet formation, and vice versa. As such, the drift reduction adjuvant composition can be selected based on the speed of the relative air flow and the angle of the relative air flow relative to the spray sheet. For example, the quantity of at least one of the polymer or the perforation-aid type adjuvant that is present in the drift reduction adjuvant composition can be decreased or increased, respectively, as the expected speed of the relative air flow increases and/or the expected angle of the relative air flow becomes closer to 90°.

In an example, the drift reduction adjuvant composition can be selected to be used when the speed of the relative air flow is less than about 35 miles per hour ("mph"), such as in ranges of about 0 mph to about 5 mph, about 2.5 mph to about 7.5 mph, about 5 mph to about 10 mph, about 7.5 mph to about 12.5 mph, about 10 mph to about 15 mph, about 12.5 mph to about 17.5 mph, about 15 mph to about 20 mph, 17.5 mph to about 22.5 mph, about 20 mph to about 25 mph, about 22.5 mph to about 27.5 mph, about 25 mph to about 30 mph, about 27.5 mph to about 32.5 mph, about 30 mph to about 35 mph, or combinations thereof. In such an example, the speed of the ambient air and/or the speed of the applicator can be less than at about 20 mph, such as ranges of about 0 mph to about 5 mph, about 2.5 mph to about 7.5 mph, about 5 mph to about 10 mph, about 7.5 mph to about 12.5 mph, about 10 mph to about 15 mph, about 12.5 mph to about 17.5 mph, or about 15 mph to about 20 mph. In such an example, the applicator can include a ground applicator, such as a tractor, truck, an individual carrying the nozzle, etc., since the lower speeds that the ground applicator moves (e.g., compared to an air applicator, such as an airplane) reduces the amount of bags that form in the spray sheet. However, it is noted that the drift reduction adjuvant can be selected to be used when the speed of the relative air flow can be greater than 35 mph (e.g., the speed of the ambient air and/or the speed of the applicator is greater than 20 mph) even though the agricultural spray is likely to form bags at such high speeds.

In an example, the drift reduction adjuvant composition can be selected to be used when the angle of the relative air flow relative to the spray sheet is an oblique angle, such as angles of about 1° to about 179°, about 5° to about 30°, about 15° to about 45°, about 30° to about 60°, about 45° to about 75°, about 60° to about 80°, about 75° to about 85°, about 80° to about 100°, about 85° to about 95°, about 95° to about 105°, about 100° to about 120°, about 105° to about 135°, about 120° to about 150°, about 135° to about 165°, or about 150° to about 175°. In such an example, at least one of the ambient air flow or the movement of the applicator exhibits an oblique angle relative to the spray sheet. The oblique angle of the relative air flow relative to the spray sheet decreases the likelihood that the relative air flow causes the spray sheet to form bags and that at least some of the droplets are formed according to the bag rupture approach to bag formation. In an example, the drift reduction adjuvant composition can be selected to be used when the angle of the relative air flow relative to the spray sheet is a perpendicular angle (e.g., 90°).

In an embodiment, the drift reduction adjuvant can be selected based on the nozzle used to dispense the agricultural spray. For example, a flat fan nozzle and/or a hollow-cone type nozzle are more likely to form droplets via the bag rupture approach than, under certain circumstances, other types of nozzles. As such, the quantity of at least one of the polymer or the perforation-aid type adjuvant that is present in the drift reduction adjuvant composition can be decreased or increased, respectively, if the agricultural spray is dispensed from a flat fan nozzle or a hollow-cone type nozzle than if the agricultural spray is dispensed from another type of nozzle.

In an embodiment, the drift reduction adjuvant can be selected based on the composition of the polymer and/or the perforation-aid type adjuvant. For example, some polymers are less likely to form droplets according to the bag rupture approach than other polymers. Similarly, some perforation-aid type adjuvant are more likely to reduce droplet formation according to the bag rupture approach than other perforation-aid type adjuvants. Additionally, a specific combination of polymers and perforation-aid type adjuvants form drift reduction adjuvant compositions that are less likely to form droplets according to the bag rupture approach than other drift reduction adjuvant compositions that include a different polymer and/or perforation-aid type adjuvant. In an example, guar gum, modified guar gum, polyacrylamide, and lecithin can be less likely to generate fine droplets via the bag rupture approach of droplet formation than at least some of the other polymers disclosed herein. As such, at least one of a quantity of the polymer that is present in the drift reduction adjuvant composition can be increased or the quantity of the perforation-aid type adjuvant can be decreased when the polymer includes at least one of guar gum, modified guar gum, polyacrylamide, or lecithin. In an example, MSO can reduce the ability of the polymer to form fine droplets via the bag rupture approach than at least some of the other perforation-aid type adjuvants disclosed herein. In other words, MSO can cause the drift reduction adjuvant composition to exhibit less bag rupture. As such, at least one of a quantity of the polymer that is present in the selected drift reduction adjuvant composition can be increased or the quantity of the perforation-aid type adjuvant can be decreased when the perforation-aid type adjuvant includes MSO.

In an embodiment, the agricultural sprays that include any of the drift reduction adjuvants disclosed herein, when dispensed from a nozzle, can form spray sheets exhibiting a thickness (e.g., viscosity and/or dimensional thickness) that is greater than a substantially similar agricultural spray that does not include the drift reduction adjuvants disclosed herein delivered under the same conditions. For example, the increased thickness of the spray sheets can resist droplet formation via the bag rupture approach since the increased thickness is less likely to form thin membranes that form bags. Instead, the increased thickness of the spray sheets are more likely to form droplets via the wave stability or perforation approaches to droplet formation.

In an embodiment, in use, the agricultural spray may be delivered from an agricultural nozzle in ground applications to produce fewer fine droplets, such as reduce the number of fine droplets by at least about 1 percentage point, at least about 5 percentage points, at least about 10 percentage points, at least about 20 percentage points, at least about 25 percentage points, at least about 50 percentage points, at least about 75 percentage points, at least about 100 percentage points, at least about 150 percentage points, at least about 200 percentage points, at least about 300 percentage points, at least about 400 percentage points, at least about 500 percentage points, at least about 600 percentage points, at least about 700 percentage points, or at least about 800 percentage points compared to a substantially similar agricultural spray that does not include the drift reduction adjuvant compositions disclosed herein delivered under the same conditions. In an embodiment, in use, the agricultural spray may be delivered from an agricultural nozzle in ground applications to either reduce, maintain or increase by up to 100 percentage points (e.g., up to 75 percentage points, up to 50 percentage points, up to 25 percentage points, or up to 15 percentage points) the number of ultra-coarse droplets compared to a substantially similar agricultural spray that does not include the drift reduction adjuvant compositions disclosed herein delivered under the same conditions. With respect to management of the level of ultra-coarse droplets produced, the increase in ultra-coarse droplets by up to 100 percentage points, and more particularly up to 50 percentage points, and more particularly up to 15 percentage points, relative to spraying the agricultural spray without the drift reduction adjuvant composition is an acceptable increase, as long as the number of fine droplets are simultaneously reduced relative to spraying the substantially similar agricultural spray.

III. Agricultural Nozzles

The agricultural nozzles that may be used to spray the drift reduction adjuvant composition or agricultural sprays that includes the drift reduction adjuvant compositions of the present disclosure may vary in size, shape, material, and other characteristics. Examples of agricultural nozzles that may be used include drift reduction nozzles, such as nozzles that produce flat fan sprays. Agricultural nozzles may include those manufactured by TeeJet (TTI 11004 nozzle, XR11002-XR TeeJet Extended Range Flat Spray Tip, AIXR11004-AIXR TeeJet Spray Tip), Hypro, Greenleaf, Wilger, Lechler, including nozzle models such as AIXR, AI, TT, UCD and so on. While in prior approaches controlling the spray spectrum of agricultural sprays using drift reduction nozzles presented challenges due drift reduction technology adjuvants actually producing fines or an excessive percentage of ultra-coarse droplets when sprayed from these nozzles, the drift reduction adjuvant compositions of the present disclosure produce efficacious sprays when sprayed from these nozzles. The nozzle classifications for the agricultural nozzles that may be used to spray the agricultural compositions include but are not limited to: extremely fine (XF), purple in color, with a VIVID of approximately 50 μm; very fine (VF), red in color, with a VIVID of less than approximately 136 μm; fine (F), orange in color, with a VIVID of approximately 136-177 μm; medium (M), yellow in color, with a VIVID of approximately 177-218 μm; ultra-coarse (C), blue in color, with a VIVID of approximately 218-349 μm; very ultra-coarse (VC), green, with a VIVID of approximately 349-428 μm; extremely ultra-coarse (EC), white in color, with a VIVID of approximately 428-622 μm; and ultra-coarse (UC), black in color, with a VIVID of greater than approximately 622

Example flow rates through the nozzles include about 0.0125 to about 2.0 gallons per minute (gpm) per nozzle. As a specific example, the flow rate of the nozzle may be variable and may range from about 0.2 to about 1.5 gpm per nozzle.

The nozzles may deliver spray at a spray angle of about 65° to about 140°, up to about 140°, about 90°, about 100°, about 110°, about 120°, about 130° or about 140°.

The spray nozzles may be operated at up to 115 psi fluid pressure, or about 15 to about 115 psi, about 30 to about 60 psi fluid pressure, or about 15, about 20, about 30, about 40, about 50, about 60, about 70, about 80, about 90, about 100, about 110 psi fluid pressure, or any integer range of the aforementioned pressure levels (e.g., about 15 to about 60 psi).

It is believed that using any agricultural nozzle with the drift reduction adjuvant compositions disclosed herein can reduce droplet formation via the bag rupture approach. However, some nozzles (e.g., flat-fan nozzles or hollow cone nozzles) may be more susceptible to forming droplets via the bag rupture approach than other nozzles and, as such, may need the drift reduction adjuvant compositions disclosed herein more than other nozzles.

IV. Agricultural Compositions

As previously discussed, the drift reduction adjuvant compositions disclosed herein can be used with any suitable agricultural composition. The agricultural composition can include at least one of a pesticide (e.g., an herbicide) or a fertilizer. Some herbicides include but are not limited to glyphosate (e.g., N-(phosphonomethyl)glycine) in various forms including in the form of a salt, ester or other derivative thereof. Examples of glyphosate products include but are not limited to: its form as a potassium salt (e.g., Roundup PowerMax® and Touchdown Total®), a dimethylamine salt (e.g., Durango® DMA®), an isopropylamine salt (e.g., Cornerstone® 5 plus), and glyphosate in combination with other pesticides such as 2,4-Dichlorophenoxyacetic acid (2,4-D) (e.g., Enlist Duo™) and with dicamba (e.g., Mon 76832 and Roundup® Xtend). Other herbicides include, but are not limited to: the sodium salt of bentazon (3-(1-methylethyl)-1H-2, 1,3-benzothiadiazin-4 (3H)-one 2,2,-dioxide) (e.g., Basagran®); diglycolamine salt of 3,6-dichloro-o-anisic acid (e.g., Sterling® Blue); 3,6-dichloro-2-methoxybenzoic acid (e.g., Dicamba, Enginia™); diclycolamine salt of dicamba (e.g., XtendiMax®); 2,4-Dichlorophenoxyacetic acid (2,4-D); 1-chloro-3-ethyl-amino-5-isopropylamino-2,4,6-triazine (Atrazine); amide herbicides; arsenical herbicides; carbamate and tiocarbamate herbicides; carboxylic acid herbicides; dinitronailine herbicides; heterocyclic nitrogen-containing herbicides; organophosphate compounds; urea herbicides; and quaternary herbicides; 5-[2-chloro-4-(trifluoromethyl)phenoxy]-N-(methylsulfonyl)-2-nitrobenzamide (Fomesafen); tembotrione (e.g., Laudis®) in various forms including in the form of a salt, ester or other derivative thereof.

Weeds that may be controlled using the herbicide compositions may include, but are not limited to: barnyard grass, green foxtail, wild oats, nightshade, velvetleaf, annual morning glory, yellow nutsedge, pigweed, downy brome.

In addition or alternatively, the herbicides may include insecticides and/or fungicides. Insecticides that may be used with the disclosed drift reduction adjuvant compositions include but are not limited to: pyrethroid insecticides (e.g., bifenthrin); pyrethrins or other botanicals (e.g. D-limonene, linalool, ryania, rotenone, eugenol (clove oil); chloronicotinyls; essential oils (e.g., lemongrass, pepper wintergreen, rosemary, cinnamon, sesame, thyme, cedar oils and capsaicin); neem oil (e.g., Azadirachtin); nicotine; microbial products (e.g., *Bacillus* thuringeinis and *Beauveria bassiana*); oxadiazines (e.g., Indoxacarb); anthranilic diamide (e.g., chlorantraniliprole); juvenile hormone mimics (e.g., fenoxycarb; pyriproxifen; methoprene; and hydroprene), pyrroles (e.g., chlorfenapyr), phenylpyrazoles (e.g., fipronil), organophosphates (e.g., malathion and chlorpyrifos), inorganics (e.g., sulfur and dormant and horticultural oils); insect growth regulators such as chitin synthesis inhibitors (e.g., hexaflumuron; noviflumuron; diflubenzuron; buprofezine; cyromazine; and halofenozide); acaricides such as miticides (e.g., avermectin) and ixodicides alone or in any combination with the compositions of the present disclosure. Fungicides that may be used with the disclosed drift reduction adjuvant compositions include but are not limited to: fluxapyroxad, pyraclostrobin, propiconazole, trifloxystrobin, prothioconazole, 1,2-propanediol, azoxystrobin (e.g. Priaxor®, Onset®, Topaz®, Headline® amp, Headline® sc, Stratego®, Quadris®) alone or in any combination with the compositions of the present disclosure.

Other pesticide additives may include nematocides, plant growth regulators and animal repellents.

In addition or alternatively, the drift reduction adjuvant compositions disclosed herein may be used with desiccants and defoliants.

It is believed that the drift reduction adjuvant compositions disclosed herein in combination with any of the pesticides, herbicides, insecticides, fungicides, pesticide additives, desiccants, and/or defoliants reduces the number of fine droplets and manages (e.g., either reduces, maintains, or increases) the number of ultra-coarse droplets compared to pesticides, herbicides, insecticides, fungicides, pesticide additives, desiccants, and/or defoliants that do not include the DRT adjuvants.

When water in an admixture containing herbicide and DRT adjuvant is hard water, water conditioners such as Class Act® NG® may be admixed in order to prevent trace impurities from binding with the herbicide (e.g., precipitating). The water conditioner includes cations and anions that bind with the impurities making them unavailable for precipitating with the herbicide, and further, the water conditioner may bind to sites on the herbicide to further prevent the impurities from antagonizing the herbicide.

V. Methods of Analyzing the Agricultural Spray

An agricultural spray that includes the drift reduction adjuvant composition disclosed herein can be analyzed. Analyzing the agricultural spray may include detecting (e.g., imaging, phase doppler particle analyzer, laser diffraction, etc.) the agricultural spray in an area proximate the nozzle or a substantially similar nozzle (e.g., the agricultural spray is tested in a wind tunnel that is the same as or substantially similar to a nozzle used to dispense the agricultural spray onto crops) such that one or more bags rupturing from a spray sheet of the agricultural spray, if present, are detected (e.g., imaged). Analyzing the agricultural spray can facilitate the selection of the drift reduction adjuvant composition.

Figure 1B:
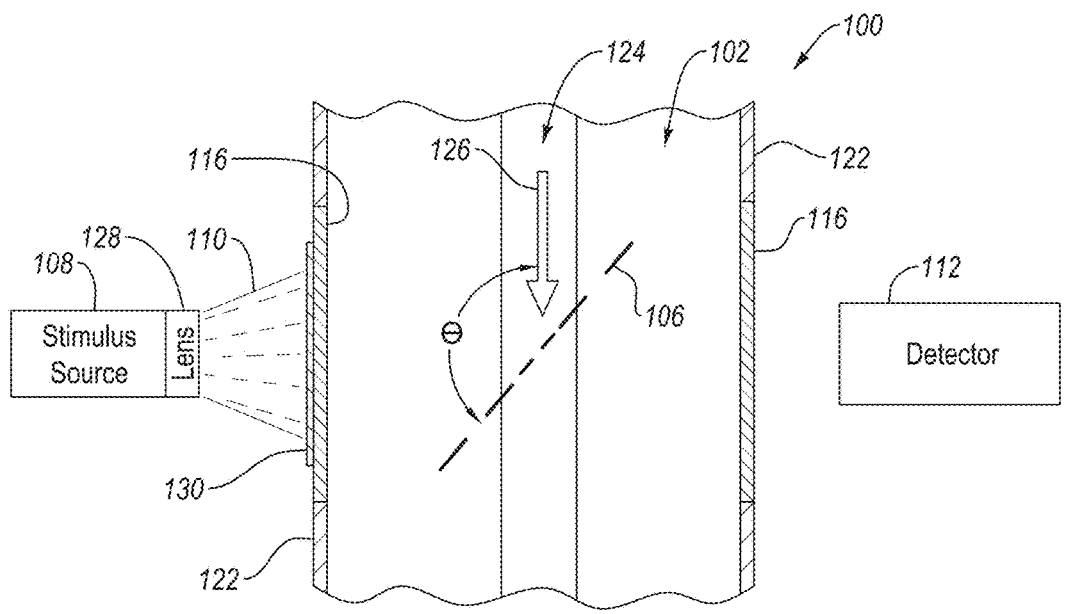

FIGS. 1A and 1B are cross-section and top plan views, respectively, of a test section 100, according to an embodiment. The test section 100 includes at least one surface defining an enclosed space 102. Generally, the enclosed space 102 is completely enclosed thereby improving uniform air flow therethrough though, in some embodiments, the enclosed space 102 may only be partially enclosed. The test section 100 includes at least one nozzle 104 disposed in the enclosed space 102 configured to dispense an agricultural spray 106 therefrom. The test section 100 also includes at least one stimulus source 108 configured to emit a stimulus 110 that illuminates at least a portion 114 (shown in phantom lines) of the agricultural spray 106 that is proximate to the nozzle 104. The test section 100 also includes a detector 112 configured to detect at least the portion 114 of the agricultural spray 106 that is proximate to the nozzle 104. The at least one surface may include at least one transparent section 116 which allows the stimulus 110 to enter the enclosed space 102 and the detector 112 to detect the portion 114 of the agricultural spray 106.

In an embodiment, as illustrated, the at least one surface (e.g., at least one wall) that defines that enclosed space 102 may include a top surface 118, an opposing bottom surface 120, and two lateral surfaces 122 extending between the top surface 118 and the bottom surface 120. Each of the top surface 118, the bottom surface 120, and the two lateral surfaces 122 may be substantially planar. However, it is noted that at least one of the top surface 118, the bottom surface 120, or the two lateral surfaces 122 may not be substantially planar. For example, as illustrated, the bottom surface 120 may define a recess 124 therein configured to receive at least a portion of the agricultural spray 106 dispensed into the enclosed space 102. Further, it is understood that the plurality of surfaces may include less than or more than four surfaces, depending on the application.

In an embodiment, the enclosed space 102 may exhibit a cross-sectional shape and cross-section dimension(s) that do not vary along a length of the enclosed space 102. Not varying the cross-sectional shape and the cross-section dimension(s) of the enclosed space 102 may increase the uniformity of the air 126 flowing through the enclosed space 102 (e.g., reduce turbulent air flow). However, in some embodiments, the enclosed space 102 may exhibit a cross-section shape and/or cross-section dimension(s) that vary along at least a portion of the length of the enclosed space 102.

In an embodiment, the at least one transparent section 116 may include a first transparent section formed in one of the two lateral surfaces 122 and a second transparent section formed in the other of the two lateral surfaces 122. The stimulus source 108 may be positioned relative to the first transparent section so the stimulus 110 enters the enclosed space 102 through the first transparent section. The stimulus 110 that enters the enclosed space 102 may illuminate at least the portion 114 of the agricultural spray 106 that is adjacent to the nozzle 104. The detector 112 may be positioned relative to the second transparent section so the detector 112 detects at least the portion 114 of the agricultural spray 106 that is adjacent to the nozzle 104 through the second transparent section. However, it is noted that the transparent section 116 and the position of the stimulus source 108 and the detector 112 may differ from the illustrated embodiment. For example, the transparent section 116 may only include a single transparent section, the transparent section 116 includes three or more transparent sections, or at least one of the stimulus source 108 or the detector 112 are disposed in the enclosed space 102.

As previously discussed, the enclosed space 102 defines an airflow path for air 126 (schematically illustrated with an arrow in FIG. 1B) to flow during operation. Generally, during operation, the average direction that the air 126 flows through the enclosed space 102 is parallel to the airflow path of the enclosed space 102. As such, as used herein, the average direction that the air 126 flows through the enclosed space 102 and the airflow path of the enclosed space 102 may be used interchangeably without limitation. However, it is noted that the average direction that the air 126 flows through the enclosed space 102 may vary slightly (e.g., less than 5° or less than 1°) from the air flow path due to turbulent air flow, recesses in the at least one surface, etc.

As previously discussed, the at least one nozzle 104 may be disposed in the enclosed space 102 and is configured to dispense the agricultural spray 106 into the enclosed space 102. In an embodiment, the nozzle 104 is positioned and configured to dispense the agricultural spray 106 in a direction at least one of parallel to gravity or perpendicular to ground (e.g., perpendicular to at least a portion of the bottom surface 120). Dispensing the agricultural spray 106 in a direction that is parallel to gravity or perpendicular to the ground mimics conventional methods of dispensing agricultural sprays on crops and is conducive to detecting the formation of bags in the spray sheet of the agricultural spray 106. However, the nozzle 104 may be positioned and configured to dispense the agricultural spray 106 in a direction not at least one of parallel to gravity or perpendicular to the ground. The nozzle 104 may be the same as or substantially similar to any of the nozzles disclosed herein.

Referring to FIG. 1B, the nozzle 104 is positioned and configured to dispense the agricultural spray 106 so at least a portion of a spray sheet of the agricultural spray 106 exhibits an spray orientation angle θ relative to the direction that the air 126 flows through the enclosed space 102. In a top plan view, the spray orientation angle θ is the angle measured clockwise from the spray sheet of the agricultural spray 106 to the average direction that the air 126 intersects the spray sheet. Unlike conventional wind tunnels, the nozzle 104 is positioned and configured so the spray orientation angle θ is non-parallel to the direction that the air 126 flows through the enclosed space 102. Selecting the spray orientation angle θ to be non-parallel to the direction that the air 126 flows through the enclosed space 102 allows the spray sheet of the agricultural spray 106 to be exposed to simulated crosswinds. It is the simulated crosswinds that may cause the spray sheet of the agricultural spray 106 to exhibit the bag rupture approach to droplet formation. For example, the spray orientation angle θ may be selected to be about 1° to about 179°. However, the spray orientation angle θ is more preferably selected to be about 10° to about 170° and, even more preferably, about 20° to about 160° or about 30° to about 150° since the spray sheet of the agricultural spray 106 is more likely to exhibit the bag rupture approach to droplet formation the closer the spray orientation angle θ is to 90°. In an example, the spray orientation angle θ may be selected to be about 10° to about 30°, about 20° to about 40°, about 30° to about 50°, about 40° to about 60°, about 50° to about 70°, about 60° to about 80°, about 70° to about 90°, about 80° to about 100°, about 90° to about 110°, about 100° to about 120°, about 110° to about 130°, about 120° to about 140°, about 130° to about 150°, about 140° to about 160°, or about 150° to about 170°.

In an embodiment, the spray orientation angle θ may be selected so the spray sheet of the agricultural spray 106 exhibits a selected orientation relative to the detector 112. In an example, the spray sheet of the agricultural spray 106 may be oriented so the image plane detected by the detector 112 is generally parallel to the spray sheet which may allow the detector 112 to detect the formation and rupture of bags along a width of the spray sheet. In an example, the spray sheet of the agricultural spray 106 may be oriented so the image plane detected by the detector 112 is generally perpendicular to the spray sheet which may allow the detector 112 to detect the edge of the spray sheet and, more particularly, the profile of the bags formed in the spray sheet.

The stimulus source 108 may include any suitable device that may illuminate the portion 114 of the agricultural spray 106 in a manner that allows the detector 112 to detect the portion 114 of the agricultural spray 106. Generally, the stimulus source 108 is an electromagnetic source configured to emit visible light. However, it is noted that the stimulus source 108 may include an electromagnetic source configured to emit non-visible light (e.g., ultraviolet light or infrared light) or another stimulus source (e.g., acoustic source). In an embodiment, the stimulus source 108 may include a single stimulus source (as shown) or a plurality of stimulus sources. In an embodiment, the stimulus source 108 is a pulsed light source, such as a pulsed laser, a pulsed LED, or a flash bulb. In an embodiment, the stimulus source 108 is a continuous light source, such as an LED light source, a halogen light source, a mercury light source, or a xenon lamp. In an embodiment, the stimulus source 108 may include configured to emit a collimated stimulus.

The type of detector 112 that is selected to detect the portion 114 of the agricultural spray 106 may depend on the stimulus 110 emitted from the stimulus source 108. For example, the detector 112 may include a camera or other detector of visible light if the stimulus 110 is visible light or may include an ultraviolet or infrared detector if the stimulus 110 is ultraviolet light or infrared light, respectively. In an embodiment, the detector 112 may include a high frame rate camera or a low frame rate camera. In an embodiment, the detector 112 may include a single detector (as shown) or a plurality of detectors. The type of detector 112 that is selected to detect the portion 114 of the agricultural spray 106 may depend on whether the detector 112 is configured to image the portion 114, using a phase doppler particle analyzer to detect the portion 114, or detect laser diffraction caused by the portion 114.

As previously discussed, the stimulus source 108 is positioned and configured to illuminate at least the portion 114 of the agricultural spray 106 and the detector 112 is positioned and configured to detect at least the portion 114 of the agricultural spray 106. In an example, the portion 114 of the agricultural spray 106 includes a region of the agricultural spray 106 initially exiting the nozzle 104 that forms the continuous sheet-like portion to define an initial spray pattern, such as a fan-shaped pattern or a cone-shaped pattern. In such an example, the portion 114 of the agricultural spray 106 may also include additional portions of the agricultural spray 106 extending from the initial spray pattern, such as ligament structures formed from the initial spray pattern. In an example, the portion 114 of the agricultural spray 106 extends from the nozzle 104 and includes the area of primary atomization and, optionally, an area of secondary atomization. In such an example, the portion 114 allows the atomization of the continuous liquid phase of the agricultural spray 106 to be detected (e.g., visually studied). In an example, the portion 114 of the agricultural spray 106 extends from the nozzle 104 until at least the continuous liquid phase of the agricultural spray 106 collapses into ligament structures. In such an example, the portion 114 may also include regions of the agricultural spray 106 after the collapse of the ligament structures. In an example, the portion 114 of the agricultural spray 106 includes all of the agricultural spray 106 except for regions of the agricultural spray 106 after substantially full and complete atomization (i.e., substantially no additional droplet formation occurs) is achieved. In an example, the portion 114 of the agricultural spray 106 extends from the nozzle 104 to about 1 to about 3 times the breakup length of the agricultural spray 106. In an example, a horizontal dimension of the portion 114 of the agricultural spray 106 is sufficient to adequately capture the entirety of the agricultural spray 106 for a given downstream length. In such an example, the horizontal dimension of the portion 114 of the agricultural spray 106 is a function of the spray angle of the nozzle 104. In an example, a horizontal dimension of the portion 114 of the agricultural spray 106 does not capture the entirety of the agricultural spray 106 for a given downstream length. In such an example, the horizontal dimension of the portion 114 may include at least 10%, at least 25%, at least 50%, at least 75%, or at least 90% of the entirety of the agricultural spray 106 for a given downstream length.

In an embodiment, the test section 100 includes one or more optical elements configured to facilitate operation of the test section 100. The one or more optical elements may include one or more lenses, one or more apertures, one or more diffusers, or any other suitable optical element. In an example, when the stimulus source 108 includes a laser, the one or more optical elements may include an aspheric lens 128 or other optical elements which causes the laser beam to diverge. In an example, the one or more optical elements may include a diffuser 130 configured soften the stimulus 110 emitted from the stimulus source 108 thereby reducing the harsh light and hard shadows detected by the detector 112 which may increase the resolution of image or signal detected by the detector 112. The diffuser 130 may be positioned between the stimulus source 108 and the agricultural spray 108, as shown, or may be positioned between the agricultural spray 106 and the detector. In an example, the one or more optical elements may include a lens (not shown) configured to collimate the stimulus 110 emitted from the stimulus source 208 since the collimating the stimulus 110 may improve the resolution of the image or signal detected by the detector 112. In an example, the one or more optical elements may include a lens (not shown) that is a collection lens or a condenser lens that causes the collimated light to converge. In such an example, the one or more optical element may also include an aperture (not shown) positioned in series with and closer to the detector than the lens. The lens and the aperture, collectively, may improve the resolution of the image or signal detected by the detector 112. In an example, the test section 100 may include at least one lens (not shown) configured to magnify the portions of the agricultural spray 106 detected by the detector 112, one or more mirrors (not shown), one or more optical filters (not shown), one or more polarizers (not shown), or any other suitable optical element.

The test section 100 may be used in any suitable wind tunnel. In an example, the test section 100 may be used in a wind tunnel that includes a blower (not shown) fluidly coupled to and positioned upstream from test section 100. The blower may include any suitable device for pushing the air 126 through the test section 100. The blower may be configured to flow the air 126 through the enclosed space 402 at any of the speeds disclosed herein. In an example, the test section 100 may be used in a wind tunnel that includes a spray particle scrubber (not shown) that is fluidly coupled to and positioned downstream from the test section 100. The spray particle scrubber may be configured to collect droplets that reach the spray particle scrubber thereby preventing the droplets from continuing down the wind tunnel. In an example, the wind tunnel includes one or more tunnels connecting the test section 100 to one or more components or regions of the wind tunnel. For instance, the one or more tunnels may fluidly couple the blower to the test section 100 and/or the test section 100 to the spray particle scrubber. Further examples of wind tunnels that may include the test section 100 are disclosed in U.S. Pat. No. 8,689,619 filed on Sep. 13, 2012, the disclosure of which is incorporated herein, in its entirety, by this reference.

The test section 100 illustrated in FIGS. 1A and 1B is merely one example of a test section that can detect the bag rupture approach to droplet formation. Other examples of test sections that can detect the bag rupture approach to droplet formation and wind tunnels including the test sections are disclosed in U.S. Patent Application No. TBD entitledTest Sections, Wind Tunnels Including the Same, and Methods of Using the Same" (Dkt. No. P278945.US.01), which was previously incorporated.

The following working examples provide further detail in connection with the specific embodiments described above.

Comparative Example 1

The agricultural spray of this Comparative Example 1 was formed by mixing XtendiMax®, Roundup® PowerMAX®, Class Act® Ridion™, and OnTarget™ together. OnTarget™ is a proprietary drift reduction adjuvant that includes at least one rheology modifier. The product use rates of Xtendi-Max® and Roundup® PowerMAX® in the agricultural spray of Comparative Example 1 were both 22 ounces per acre. The amounts of Class Act® Ridion™ and OnTarget™ in the agricultural spray of Comparative Example 1 were 1.0 volume % and 0.5 volume %, respectively. The product use rate of Comparative Example 1 was 15 gallons per acre.

The test section of the wind tunnel shown in FIGS. 1A-1B was used to test the agricultural spray of Comparative Example 1. The nozzle of the testing section was a Wilger UR 11004. The agricultural spray of Comparative Example 1 was emitted from the nozzle at 40 pounds per square inch. The air flowing through the test section was held at a constant speed that simulated an ambient air speed of 15 mph and a speed of the applicator of 15 mph. The spray orientation angle θ between air flowing through the test section and the spray sheet was 45°.

Figure 2:
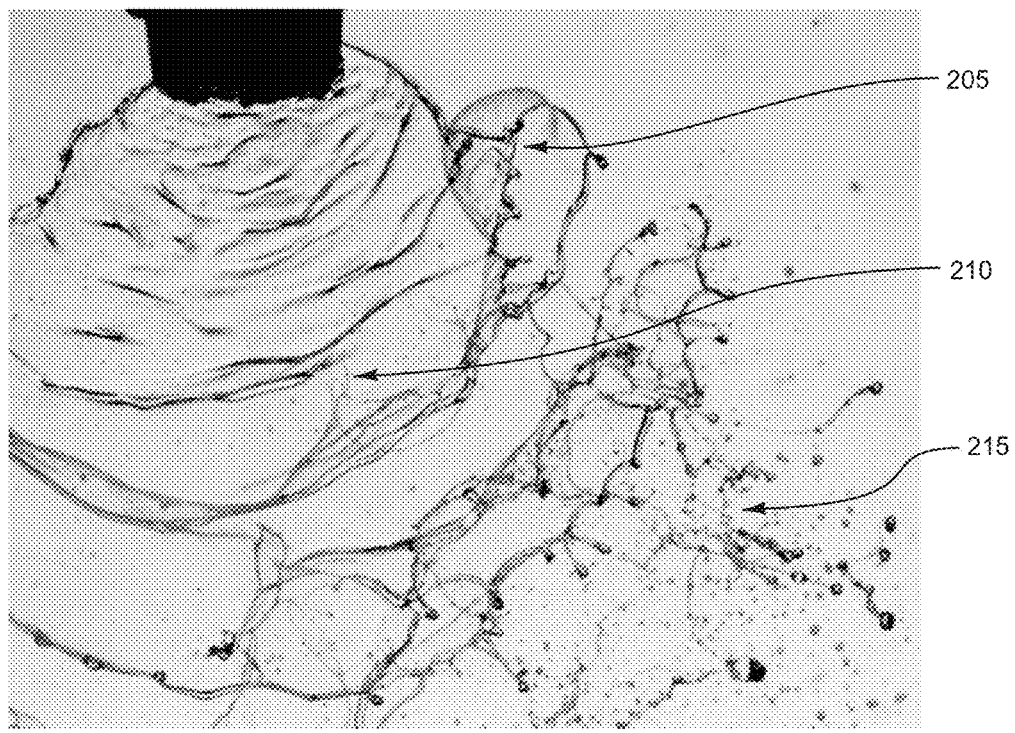
FIG. 2 is an image of the spray sheet of agricultural spray of the Comparative Example 1 near the nozzle experiencing the bag rupture approach to droplet formation.

FIG. 2 is an image of the spray sheet of agricultural spray of the Comparative Example 1 near the nozzle experiencing the bag rupture approach to droplet formation. In FIG. 2, a bag is shown that has been formed in the agricultural spray of Comparative Example 1 (indicated with arrow 205). FIG. 2 also shows a bag that is in the process of rupturing (indicated with arrow 210). Droplets formed from a ruptured bag (indicated with arrow 215) is also shown in FIG. 2.

Working Example 1

An agricultural spray of the Comparative Example 1 was provided. InterLock®, a propriety adjuvant that includes at least one perforation-aid type adjuvant, was added to the agricultural spray to form the agricultural spray of Working Example 1. The agricultural spray of Working Example 1 was then sprayed into the test section of the wind tunnel shown in FIGS. 1A-1B using the same method as the agricultural spray of Comparative Example 1.

Figure 3:
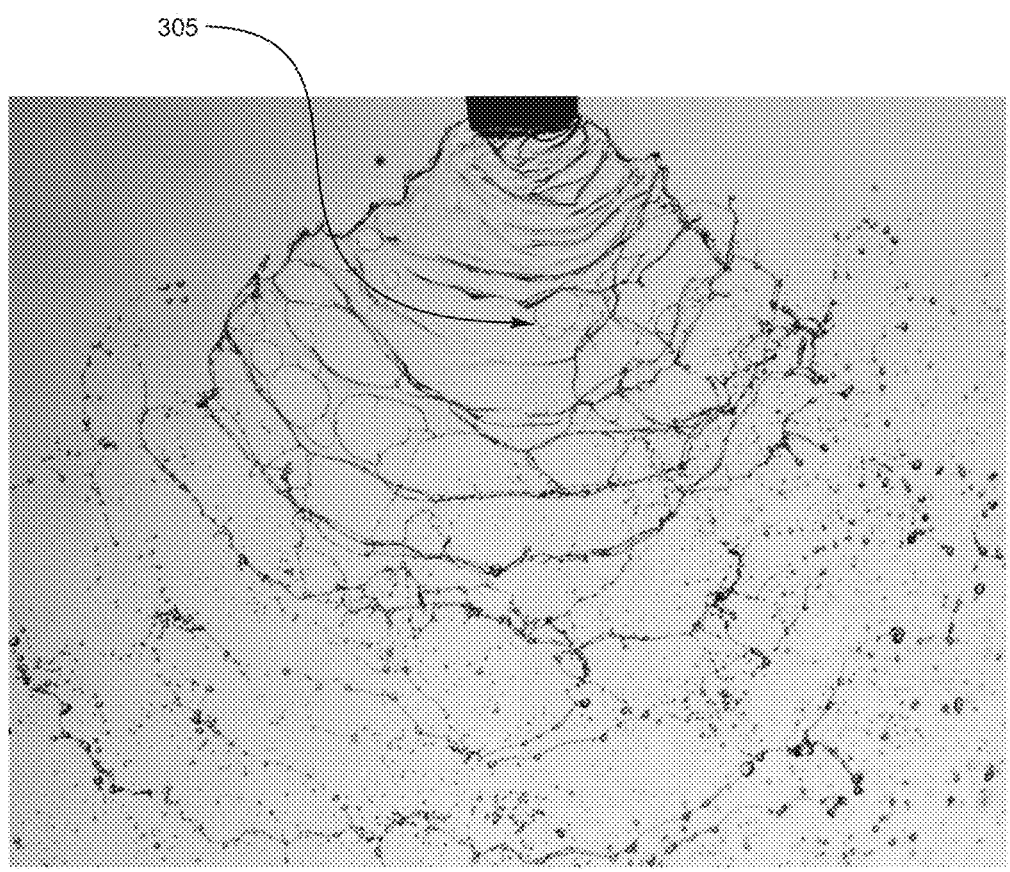
FIG. 3 is an image of the spray sheet of the agricultural spray of Working Example 1 near the nozzle.

FIG. 3 is an image of the spray sheet of the agricultural spray of Working Example 1 near the nozzle. FIG. 3 illustrates that the agricultural spray of Working Example 1 exhibited little to no bag formation. Instead, FIG. 3 illustrates that the spray sheet formed from the agricultural spray of Working Example 1 formed perforations therein (indicated with arrow 305) instead of bags.

Comparative Example 2

The agricultural spray of Comparative Example 2 was formed by mixing Engenia® and Roundup® PowerMax. The product use rates of Engenia® and Roundup Power-Max® in the agricultural spray of Comparative Example 2 were both 13 and 32 ounces per acre, respectively. The product use rate of Comparative Example 1 was 15 gallons per acre.

The test section of the wind tunnel shown in FIGS. 1A-1B was used to test the agricultural spray of Comparative Example 2. The nozzle of the test section was a TTI11004. The agricultural spray of Comparative Example 2 was emitted from the nozzle at 63 pounds per square inch. The air flowing through the test section was held at a constant speed that simulated an ambient air speed of 15 mph and a speed of the applicator of 15 mph. The spray orientation angle θ between air flowing through the test section and the spray sheet was 45°. Testing indicated that agricultural spray of Comparative Example 2 did not exhibit the bag rupture approach to droplet formation since the agricultural spray of Comparative Example 2 did not include a polymer.

Comparative Example 3

The agricultural spray of Comparative Example 3 was substantially the same as the agricultural spray of Comparative Example 2 except that OnTarget™ was added to the agricultural spray of Comparative Example 3. The amount of OnTarget™ in the agricultural spray of Comparative Example 2 was 1.0 volume %. The agricultural spray of Comparative Example 3 was tested using the same conditions as the agricultural spray of Comparative Example 2. The agricultural spray of Comparative Example 3 did exhibit the bag rupture approach to droplet formation thereby illustrating that polymers, such as rheology modifiers, can cause the agricultural spray to exhibit the bag rupture approach to droplet formation.

Working Example 2

The agricultural spray of Working Example 2 was substantially the same as the agricultural spray of Comparative Example 3 except that Interlock® (i.e., a perforation-aid type adjuvant that includes a proprietary amount of MSO) was added to the agricultural spray of Comparative Example 2. The product use rate of Interlock® in the agricultural spray of Working Example 2 was 2 ounces per acre. The agricultural spray of Working Example 2 was tested using the same conditions as the agricultural spray of Comparative Example 2. The agricultural spray of Working Example 2 did not exhibit the bag rupture approach to droplet formation thereby illustrating that the perforation-aid type adjuvant can prevent the bag rupture approach to droplet formation.

Working Example 3

The agricultural spray of Working Example 3 was substantially the same as the agricultural spray of Comparative Example 3 except that a perforation-aid type adjuvant including paraffinic oil was added to the agricultural spray of Working Example 3. The agricultural spray of Working Example 3 was tested using the same conditions as the agricultural spray of Comparative Example 2. The agricultural spray of Working Example 3 did not exhibit the bag rupture approach to droplet formation thereby illustrating the perforation-aid type adjuvant can prevent the bag rupture approach to droplet formation.

We claim:
1. A method to reduce bag rupture in an agricultural spray dispensed from a nozzle, the method comprising:
    dispensing the agricultural spray from the nozzle, the agricultural spray comprising:
        water;
        at least one polymer; and
        at least one perforation-aid type adjuvant; and
    wherein the agricultural spray exhibits fewer fine droplets exhibiting a diameter less than about 150 μm formed via the bag rupture approach to droplet formation than a similar agricultural spray that does not comprise the at least one perforation-aid type adjuvant as determined by an analysis of the agricultural spray;
    wherein the analysis of the agricultural spray comprises detecting at least a portion of the agricultural spray adjacent to the nozzle or a similar nozzle such that one or more bags rupturing from the agricultural spray, if present, are detected, each of the one or more bags comprising a thin membraned semi-spherical protrusion extending from the agricultural spray, wherein the portion of the agricultural spray adjacent to the nozzle includes a region of the agricultural spray initially exiting the nozzle that forms a continuous sheet-like portion defining an initial spray pattern.
2. The method of claim 1, wherein the at least one polymer comprises at least one rheology modifier.
3. The method of claim 2, wherein the at least one rheology modifier includes at least one of guar gum, modified guar gum, polyacrylamide, or lecithin.
4. The method of claim 1, wherein the at least one polymer comprises lecithin.
5. The method of claim 1, wherein the at least one perforation-aid type adjuvant comprises at least one oil emulsion and at least one surfactant.
6. The method of claim 5, wherein the at least one oil emulsion comprises at least one modified seed oil.
7. The method of claim 1, wherein the at least one perforation-aid type adjuvant forms about 0.04% (v/v) to about 1.0% (v/v) of the agricultural spray.
8. The method of claim 1, wherein the at least one perforation-aid type adjuvant comprises a suspension type herbicide.
9. The method of claim 1, wherein the at least one perforation-aid type adjuvant comprises at least one non-ionic surfactant.
10. The method of claim 1, wherein the agricultural spray comprises at least one agricultural composition, the at least one agricultural compositing including at least one pesticide and/or at least one fertilizer.
11. The method of claim 1, wherein dispensing the agricultural spray from the nozzle comprises dispensing the agricultural spray from a nozzle in a direction that is perpendicular to the ground.
12. The method of claim 1, wherein dispensing the agricultural spray from the nozzle comprises dispensing the agricultural spray from the nozzle in a vertical direction and exposing the agricultural spray to air flowing in a direction that is parallel to the ground.
13. The method of claim 12, wherein, the agricultural spray is dispensed from the nozzle in a sheet-like shape, and wherein air flowing in the direction that is parallel to the ground intersects the sheet-like shape of the agricultural spray at an oblique angle.
14. The method of claim 12, wherein dispensing the agricultural spray from the nozzle comprises analyzing the agricultural spray by dispensing the agricultural spray in an enclosed space of a test section of a wind tunnel, wherein analyzing the agricultural spray further comprises:
    emitting a stimulus into the enclosed testing region towards at least the portion of the agricultural spray adjacent to the nozzle; and
    detecting at least the portion of the agricultural spray adjacent to the nozzle.
15. The method of claim 1, wherein dispensing the agricultural spray from the nozzle comprises dispensing the agricultural spray from a ground applicator that includes the nozzle, the ground applicator moving at a speed of about 20 miles per hour or less.
16. The method of claim 1, wherein the agricultural spray exhibits at least 50% fewer of the fine droplets formed via the bag rupture approach to droplet formation than the similar agricultural spray that does not comprise the at least one perforation-aid type adjuvant.
17. The method of claim 1, wherein the agricultural spray exhibits at least 90% fewer of the fine droplets formed via the bag rupture approach to droplet formation than the similar agricultural spray that does not comprise the at least one perforation-aid type adjuvant.
18. The method of claim 1, wherein the nozzle is a flat-fan nozzle.
19. A method to reduce bag rupture in an agricultural spray dispensed from a nozzle, the method comprising:
    dispensing the agricultural spray from the nozzle, the agricultural spray exhibiting a sheet-like shape, the agricultural spray comprising:
        water;
        at least one drift reduction adjuvant composition comprising at least one rheology modifier and at least one perforation-aid type adjuvant; and
        at least one agricultural composition comprising at least one pesticide and/or at least one fertilizer;
    wherein the agricultural spray exhibits fewer fine droplets exhibiting a diameter less than about 150 μm formed via the bag rupture approach to droplet formation than a similar agricultural spray that does not comprise the at least one perforation-aid type adjuvant as determined by an analysis of the agricultural spray;
    wherein the analysis of the agricultural spray comprises detecting at least a portion of the agricultural spray adjacent to the nozzle or a f such that one or more bags rupturing from the agricultural spray, if present, are detected, each of the one or more bags comprising a thin membraned semi-spherical protrusion extending from the agricultural spray, wherein the portion of the agricultural spray adjacent to the nozzle includes a region of the agricultural spray initially exiting the nozzle that forms a continuous sheet-like portion defining an initial spray pattern.

20. The method of claim 19, wherein the agricultural spray exhibits at least 50% less bag rupture when dispensed from the nozzle than the similar agricultural spray that does not comprise the at least one perforation-aid type adjuvant.

21. A method to reduce bag rupture in an agricultural spray dispensed from a flat-fan nozzle, the method comprising:
   dispensing the agricultural spray from the flat-fan nozzle in a direction that is perpendicular to a ground, the agricultural spray comprising:
      water;
      at least one rheology modifier comprising at least one of guar gum, modified guar gum, polyacrylamide, or lecithin;
      at least one perforation-aid type adjuvant comprising at least one surfactant and at least one of a modified seed oil or a paraffinic oil; and
      at least one agricultural composition comprising at least one pesticide and/or at least one fertilizer;
   wherein the agricultural spray exhibits at least 50% fewer fine droplets exhibiting a diameter less than about 150 µm formed via the bag rupture approach to droplet formation than a similar agricultural spray that does not comprise the at least one perforation-aid type adjuvant as determined by an analysis of the agricultural spray;
   wherein the analysis of the agricultural spray comprises detecting at least a portion of the agricultural spray adjacent to the nozzle or a similar nozzle such that one or more bags rupturing from the agricultural spray, if present, are detected, each of the one or more bags comprising a thin membraned semi-spherical protrusion extending from the agricultural spray, wherein the portion of the agricultural spray adjacent to the nozzle includes a region of the agricultural spray initially exiting the nozzle that forms a continuous sheet-like portion defining an initial spray pattern.

* * * * *

UNITED STATES PATENT AND TRADEMARK OFFICE
CERTIFICATE OF CORRECTION

PATENT NO. : 10,499,560 B1
APPLICATION NO. : 16/198384
DATED : December 10, 2019
INVENTOR(S) : Bissell et al.

It is certified that error appears in the above-identified patent and that said Letters Patent is hereby corrected as shown below:

In the Specification

At Column 17, Line 12:
"with a VIVID of approximately 50 µm; very fine (VF), red in color, with a VIVID of less than approximately 136 µm; fine (F), orange in color, with a VIVID of approximately 136-177 µm; medium (M), yellow in color, with a VIVID of approximately 177-218 µm; ultra-coarse (C), blue in color, with a VIVID of approximately 218-349 µm; very ultra-coarse (VC), green, with a VIVID of approximately 349-428 µm; extremely ultracoarse (EC), white in color, with a VIVID of approximately 428-622 µm; and ultra-coarse (UC), black in color, with a VIVID of greater than approximately 622."

Should read:
--with a VMD of approximately 50 µm; very fine (VF), red in color, with a VMD of less than approximately 136 µm; fine (F), orange in color, with a VMD of approximately 136-177 µm; medium (M), yellow in color, with a VMD of approximately 177-218 µm; ultra-coarse (C), blue in color, with a VMD of approximately 218-349 µm; very ultra-coarse (VC), green, with a VMD of approximately 349-428 µm; extremely ultra-coarse (EC), white in color, with a VMD of approximately 428-622 µm; and ultra-coarse (UC), black in color, with a VMD of greater than approximately 622 µm.--

Signed and Sealed this
Fourth Day of February, 2020

Andrei Iancu
*Director of the United States Patent and Trademark Office*